United States Patent [19]

Mälson et al.

[11] Patent Number: 4,772,419

[45] Date of Patent: Sep. 20, 1988

[54] SHAPED ARTICLE AND PROCESSES FOR ITS PREPARATION

[75] Inventors: Tomas Mälson, Uppsala; Leif G. Ahrgren, Örbyhus; Anthony N. de Belder, Uppsala, all of Sweden

[73] Assignee: Pharmacia AB, Uppsala, Sweden

[21] Appl. No.: 831,540

[22] Filed: Feb. 21, 1986

[30] Foreign Application Priority Data

Mar. 1, 1985 [SE] Sweden ................. 8501022

[51] Int. Cl.$^4$ ............................................. C08B 37/08
[52] U.S. Cl. ................. 252/315.1; 536/55.1; 424/423; 424/427
[58] Field of Search ............ 252/315.3; 604/891; 536/55.1; 424/423, 427; 435/240.21

[56] References Cited

U.S. PATENT DOCUMENTS

| 2,599,172 | 6/1952 | Hadidian | 536/55.1 |
| 2,824,092 | 2/1958 | Thompson | 252/315.3 X |
| 2,926,177 | 2/1960 | Linn | 536/55.1 X |
| 3,211,616 | 10/1965 | Yosizawa | 536/55.1 |
| 3,396,081 | 8/1968 | Billek | 536/55.1 X |
| 4,468,334 | 8/1984 | Cox et al. | 252/315.3 X |
| 4,613,665 | 9/1986 | Larm | 536/55.1 X |
| 4,615,697 | 10/1986 | Robinson | 604/891 X |

FOREIGN PATENT DOCUMENTS

| 84999 | 8/1983 | European Pat. Off. | 536/55.1 |
| 28090 | 7/1972 | Japan | 252/315.3 |
| 145036 | 8/1984 | Japan | 252/315.3 |

*Primary Examiner*—Matthew A. Thexton
*Assistant Examiner*—Catherine S. Kilby
*Attorney, Agent, or Firm*—Fred Philpitt

[57] ABSTRACT

A shaped article based upon cross-linked, possibly derivatized hyaluronic acid or a salt thereof is characterized in that it has a dry matter content of at least 65 percent by weight and a tensile strength of at least 2 N/cm$^2$. The shaped article may be prepared by pressure-drying or freeze-drying a corresponding hyaluronic acid gel.

14 Claims, No Drawings

SHAPED ARTICLE AND PROCESSES FOR ITS PREPARATION

The present invention relates to a shaped hyaluronic acid product having improved handling properties. The invention also relates to processes for producing such a shaped product.

Hyaluronic acid is a high viscosity polysaccharide naturally present in the tissues of human beings and animals and composed of alternating glucuronic and D-acetylglucosamine units and having an average molecular weight $M_w$ in the range of 20,000 to 5,000,000 depending on the source and method of purification. Inter alia, it is a major component of synovial fluid and the vitreous body of the eye. Due to its natural bioresorbability and the absence of toxicologic and immunologic effects it has found medical use, i.a. as an aid in eye operations and to prevent adhesion and accretion of tissues after surgical operations. In these cases the hyaluronic acid has been applied in the form of a viscous aqueous solution. For this reason the use thereof has, however, been restricted to such cases where the requirements as to mechanical stability have been small, and the duration of the protective effect has been shorter than desired.

An improvement in these respects has been achieved with a gel product of cross-linked hyaluronic acid. The preparation of such gels and their use as resorbable implants are described in our International patent application publication No. WO 86/00079 and application No. PCT/SE85/00282, respectively (the full disclosures of which are incorporated herein by reference). The gel products may be produced in a great number of various shapes depending on the field of application, e.g., as thin layers, plates, bar or tubes, and may be sterilized and autoclaved. They are intended to be applied as a gel swollen in buffered physiological saline and having a hyaluronic acid concentration corresponding to a dry matter content in the range of 0.1–50 percent by weight. Examples of situations where it is meant that such gel implants may be used are abdominal operations, operations of the urogenital tracts, nerve surgery, joint operations and opthalmological operations.

Also these gel products have, however, several disadvantages. For example, they must be stored swollen in physiological saline, and their strength is very poor. Therefore they easily break when being applied, particularly when handled with a pair of forceps or when sewn.

According to the present invention it has now been found that by at least substantially reducing the water content of a gel of cross-linked hyaluronic acid a product may be obtained which has considerably improved handling properties and which is excellently suitable for use as a resorbable implant, for example, for preventing the adhesion and accretion of tissues. In comparison with the gel products the novel dried forms have a significantly greater tensile strength and tearing resistance and may be made very thin and flexible. Nor need they be stored in physiological saline. Also after reswelling the products according to the invention have an improved strength compared with a gel product which has not been dried or dehydrated in accordance with the invention.

According to the present invention there is consequently provided a shaped article based upon cross-linked, possibly derivatized hyaluronic acid or a salt thereof, e.g., the sodium salt, which is characterized in that it in a substantially unswollen state has a dry matter content of at least 65 percent by weight and a tensile strength of at least $2N/cm^2$.

By "derivatized hyaluronic acid" is meant that hydroxy, carboxyl and/or amino functions of the hyaluronic acid may be etherified, esterified, amidated, acetalized, ketalized, etc.

The cross-linking degree may vary depending i.a. on the desired degradation time in the human or animal body. The content of cross-linking agent is generally in the range of 0.002 to 4 moles per mole of repeating unit of the hyaluronic acid. The cross-linking groups are per se not critical for the invention, and examples of suitable cross-linking agents will be mentioned below.

The dry matter content of the hyaluronic acid product according to the invention is preferably between 65 and 99 percent by weight, particularly between 85 and 98 percent by weight.

The tensile strength of the hyaluronic acid product according to the invention is preferably greater than 50 $N/cm^2$ and particularly greater than 100 $N/cm^2$, especially greater than 1000 $N/cm^2$.

The reswelling degree of the hyaluronic acid products depends i.a. on the method of preparation and the cross-linking degree, but it is preferably less than about 10 times, particularly less than about 5 times, and especially less than about twice the initial "dried" volume.

The novel hyaluronic acid products may be produced in a great number of shapes, such as plates, sheets, tubes, bars, spheres, etc., or any other suitable shape for any particular application. The applicability is, of course, not restricted to preventing the adhesion or accretion of tissues after surgical operations, but the hyaluronic acid products of the invention may be used in many other connections where it is desired to apply a resorbable product in or on an animal or human body. They may be applied in dry form or completely or partially swollen in physiological saline as desired.

According to the invention the above described hyaluronic acid products may be prepared from a gel of cross-linked, possibly derivatized hyaluronic acid or a salt thereof, by subjecting the gel to a drying or dehydrating step under certain conditions. The dehydration or drying should thus be performed in a controlled manner such that the water removal takes place substantially uniformly over the gel surface.

Preferably, the dehydrated or dried gel is subjected to a subsequent heat treatment to increase the wet strength of the material, i.e. the strength after swelling, as will be described further below.

The gels of cross-linked hyaluronic acid used as the starting material may be prepared in per se known manner, e.g., as described in the above mentioned International patent application publication No. WO86/00079 and application No. PCT/SE85/00282. In such a case one may, e.g., start from a hyaluronic acid having an average molecular weight ($M_w$) in the range of 500,000 to 3,000,000 or a salt thereof, e.g. the sodium salt, for example, such a highly purified product as is described in the U.S. Pat. No. 4,141,973. Suitable cross-linking reagents may readily be selected by a person skilled in the art and may be bi- or polyfunctional cross-linking reagents producing, e.g., ether, ester or amide linkages. Exemplary of such cross-linking agents are di- or polyfunctional epoxides, such as, e.g., 1,4-butanedioldiglycidyl ether (BDDE), 1,2-ethanedioldiglycidyl ether (EDDE), 1-(2,3-epoxypropyl)-2,3-epoxycyclohexane, N,N-diglycidylaniline and epoxy-substituted pentaerythritol.

The cross-linking reaction may be performed in an acid medium in the presence of an acid catalyst, as described in the above mentioned International patent application publication No. WO 86/00079, or in an alkaline medium, as described in the above mentioned International patent application No. PCT/SE85/00282. The reaction is preferably performed such that the cross-linking agent content of the end product is from 0.02 to 0.6 moles per mole of repeating unit of the hyaluronic acid, particularly 0.1 to 0.5 moles per mole.

The above described gels of cross-linked hyaluronic acid are, however, only examples, and for the objects of the invention cross-linked hyaluronic acid gels prepared in other ways may be used just as well.

According to a first embodiment of the process the drying of the cross-linked hyaluronic acid gel is performed by subjecting the latter to a vacuum less than about 5 mm Hg. In so far as the hyaluronic acid gel contains salts, e.g., by having been stored in physiological saline, it should first be desalted. Such a desalting step reduces the crack formation and provides a greater flexibility of the end product. This vacuum drying is in fact a kind of freeze-drying, the evaporation of water from the surface of the gel material providing the necessary cooling. The drying process may therefore advantageously be performed in a conventional freeze-drying unit. The gel material, e.g., in the form of a gel plate, is in such a case, in contrast to conventional feeze-drying, introduced into the freeze-drying unit without any preceding freezing, suitably at room temperature, after which the air is evacuated. The gel material is suitably supported on a porous support, such as, e.g., a net or the like, such that the freeze-drying may take place over substantially the entire gel surface. Due to the fact that the material is not frozen before the air is evacuated the growth of large ice crystals from the cooling surface during the cooling is prevented, which growth would result in the gel freeze-bursting. Instead very small ice crystals are obtained within the gel, providing a uniform, flexible and crack-free product. In this modified freeze-drying process also the original shape of the hyaluronic acid gel is maintained, e.g. tubular, rod-shaped, spherical, etc.

The products obtained by the above described freeze-drying of hyaluronic acid gels generally have a spongy structure. It has been found that the mechanical properties of the product, e.g. the bending strength, may be improved if the dried product is compressed, e.g. by rolling, such that the spongy structure is broken down. The compression pressure, or roll pressure, is suitably between 10 and $10^5$ kPa. The pressure surfaces between which the dried product is compressed should, however, not contain iron, which was proved to catalyze the degradation of hyaluronic acid. Such subsequent rolling of the product may in a simple procedure be effected by means of a round bar of glass, titanium, Teflon® or other suitable material using, e.g., a glass plate as a support. It may, however, be preferred to use an apparatus of calender or mangle type or the like having rolls of a suitable material.

According to a second embodiment of the process the drying or dehydration is performed by compressing the gel material, e.g., in the form of a plate, between two pressure surfaces while applying a compressive force on one or both surfaces. Preferably, at least one pressure surface is of a porous nature, having a sufficient open porosity to permit the passage of fluid squeezed out from the gel through the surface. On the other hand, the pore size should not be so large that the hyaluronic acid gel material will penetrate into the openings to any appreciable extent during the compression. The term porous is in this connection to be understood in a broad sense and is, e.g., also to comprise materials of a reticulate structure, of dialysis tube type, elements having closely spaced apertures or openings, etc. In a simple embodiment the pressure surfaces may consist of two net members, e.g., nylon nets. Fluid squeezed out from the hyaluronic acid gel may, depending on the design of the pressure surfaces, be removed by evaporation and/or aspiration, e.g., by a layer of another porous material, such as fritted glass, applied to the rear faces of the pressure surface members. The compression pressure is generally in the range of $10-10^5$ kPa, but is preferably 100–5000 kPa, particularly 200–1000 kPa. If desired, one may in the compression process start with a lower pressure, and increase it successively. The operation is suitably performed at about ambient temperature.

In comparison with the first mentioned modified freeze-drying process this second embodiment of the process, or pressure-drying, does not require any preceding desalting of the gel material and therefore offers increased possibilities of varying the density of the starting material and thereby the properties of the product.

As mentioned above the properties of the dried products obtained may be improved by a subsequent heat treatment. In case the above mentioned freeze-drying process is accompanied by a compression step, such a heat treatment is suitably performed after the compression or rolling. The heat treatment is suitably performed at a temperature of 50°–120° C. for 1–24 hours, preferably at 100°–130° C. for 5–15 hours. In addition to the fact that such a heat treatment increases the wet strength of the material, the swelling thereof in physiological saline is usually minimized.

The invention will now be illustrated further by means of some particular, non-limiting examples.

PREPARATION OF HYALURONIC ACID GELS

I. GEL PLATES OF TYPE A (ACID CATALYSIS)

A1. 20.0 ml of water were added to 2.0 g of salt-free high-molecular sodium-hyaluronate (average molecular weight ($M_w$) about $3 \times 10^6$) in a plastic test tube.

The hydraulic acid was then allowed to swell for a couple of hours, whereupon the substance was dissolved by careful treatment with a glass rod. When a clear homogeneous solution had been obtained, 1.0 ml of concentrated acetic acid was added and incorporated for about 10 minutes to homogeneity. 2.0 ml of 1,4-butanedioldiglycidyl ether (BDDE) were then added and thoroughly intermixed. The tube was then vigorously centrifuged to obtain a homogeneous gel without air bubbles.

The gel was then pressed out on thick glass plates coated with a thin plastic sheet. A 0.33 mm thick plastic frame was applied around the outer edges of the glass plate. A plastic sheet was then placed upon the gel which was rolled out to the thickness of the frame. When rolling it out care was taken to obtain a homogeneous cake which was as free from air bubbles as possible. When necessary the glass plate was heated from below to reduce the viscosity of the gel. A glass plate was placed upon the gel cake, and the package was sealed with adhesive tape. It was then heated at about 50° C. in a heating chamber overnight with a weight placed on top thereof.

Then the upper glass plate, the upper plastic sheet and the frame were removed. The lower plastic sheet with the gel was placed up and down in 4 liters of water in a washing equipment consisting of a plastic dish having a perforated bottom covered with a nylon net and placed in second plastic dish with a magnetic stirrer. When the gel had been released from the plastic sheet, the latter was removed and the gel washed 4 times with 4 liters of water. The gel was then transferred to a glass plate, and gel plates of 2.5×5 cm were punched out. The gel plates were then transferred into wide-mouthed glass flasks (3 in each), to which about 25 ml of sterile 0.9% physiological saline were added.

A2. A second set of gel plates were prepared in the same way as above, the added amount of the cross-linking agent BDDE, however, being changed to 1.0 ml.

II. GEL PLATES OF TYPE B (BASIC CATALYSIS)

B1. 18.75 ml of 0.5% NaOH were added to 2.5 g of salt-free high-molecular sodium hyaluronate (average molecular weight about $3 \times 10^6$) in a plastic test tube, and the mixture was stirred with a glass rod until a clear homogeneous solution was obtained. 1874 $\mu$l of BDDE were then added and thoroughly intermixed. The tube was then vigorously centrifuged to obtain a homogeneous gel without air bubbles. The gel was pressed out on glass plates and heat treated as described in section I above, however, wih heating for only 4 hours at 50° C., and it was then left at ambient temperature overnight.

The gel was then washed as in Section I above with 4×4 liters of water, 300 $\mu$l of concentrated acetic acid being added in the first two water washings. 2.5×5 cm plates were then cut out in the same way as described in section I above. The plates were transferred into wide-mouthed glass flasks (3 in each), to which about 25 ml of sterile 0.9% physiological saline buffered to pH 72 were added.

B2. A second set of gel plates were prepared in the same way as above, the added amount of the cross-linking agent BDDE, however, being changed to 937 $\mu$l.

The gel plates of types A and B prepared as above, hereinafter referred to as A1 and A2 and B1 and B2, respectively, were used as starting materials for the preparation of the dehydrated hyaluronic acid gel products according to the invention as described in the following Examples 1-12.

EXAMPLE 1

A gel plate of type A1 prepared according to process I above was desalted in 200 ml of distilled water for two hours. The greatly swollen plate was transferred to a nylon fabric (mesh width 25 $\mu$m) stretched across a tank. The excess of water was drawn off with a piece of filter paper, and the tank was placed in a freeze-drying unit maintained at ambient temperature. The air was then evacuated, the water of the gel freezing at about 0.6 kPa. Freeze-drying was allowed to proceed overnight. A dry porous plate of approximately the same thickness as the starting material was obtained.

EXAMPLE 2

The porous plate obtained in Example 1 was rolled out with a glass rod (10 mm diameter) against a glass plate by applying a compressive force of about 500N. A thin sheet of a paper-like structure was obtained.

EXAMPLE 3

The rolled out plate obtained in Example 2 was heat treated for 5 hours at 110° C. in a heating chamber.

EXAMPLE 4

A gel plate of type A1 prepared according to process I above was desalted in 200 ml of water for two hours. It was then placed between two nylon nets having a mesh width of 25 $\mu$m. About 20 layers of filter paper were placed on each side thereof, and the assembly was compressed with a 10 kg weight. After 20 hours the weight was removed, and the dry plate was removed from the nylon nets. A partially transparent sheet of a cellophane-like structure was obtained.

EXAMPLE 5

The process of Example 1 was repeated, however, using a gel plate of type B1. A dry porous plate of approximately the same thickness as the starting material was obtained.

EXAMPLE 6

The porous plate obtained in Example 5 was rolled out with a glass rod (10 mm diameter) against a glass plate by applying a compressive force of about 500N. A thin sheet of a paper-like structure was obtained.

EXAMPLE 7

The rolled out plate obtained in Example 6 was heat treated for 5 hours at 110° C. in a heating chamber.

EXAMPLE 8

The process of Example 4 was repeated, however, using a gel plate of type B1 and without any desalting of the gel plate. A partially transparent sheet of a cellophane-like structure was obtained.

EXAMPLE 9

The process of Examples 1 and 2 were repeated, however, using a gel plate of type A2. A thin sheet of a paper-like structure was obtained.

EXAMPLE 10

The process of Example 4 was repeated but with reversal of a gel plate of type A2 and without any desalting of the gel plate. A partially transparent sheet of a cellophane-like structure was obtained.

EXAMPLE 11

The process of Example 1 and 2 were repeated, however, using a gel plate of type B2. A thin sheet of a paper-like structure was obtained.

EXAMPLE 12

The process of Example 4 was repeated, however, using a gel plate of type B2 and without any desalting of the gel plate. A partially transparent sheet of a cellophane-like structure was obtained.

The water content, cross-linking degree and content of sodium hyaluronate were determined for the dry plates obtained in Examples 1-12. The water content was determined by extraction with dimethyl sulphoxide and gas-liquid chromatography (GLC). The content of cross-linking agent, i.e. BDDE residues in the products, was determined by NMR ('H). The remainder of the plate material was assumed to consist of sodium hyaluronate.

Further, the tensile strength and tear resistance were determined for each of the gel plates as well as the dried plates or sheets as follows.

The tensile strength was measured on 0.5-1 cm wide strips of the dried plates or sheets with a strain gauge at a pulling rate of 1 cm/minute.

The tear resistance was determined with a method similar to that usually used for measuring the tear resistance of paper. The ends of a 15 mm wide strip of the plate or sheet were secured obliquely relative to each other such that the end edges formed an angle of 40°. Hereby only one long side of the strip was stretched when applying a tensile force in the longitudinal direction of the strip. A small V-shaped cut was made in this side edge of the strip with a razor blade, whereupon the force required to tear the material apart was measured. The pulling rate was 1 cm/min. The result was given as the initial tear resistance, i.e. the force required to initiate the tearing process.

Also the swelling properties of the products were determined, the dried plates being allowed to swell for 20 minutes in 0.9% physiological saline. The thickness before and after the swelling was determined as well as the swelling in length and width. Further, the water absorption was determined by weighing the plates or sheets before and after swelling.

All the test results are summarized in Table I below.

TABLE I

| Product | Water content (wt. %) | BDDE residues (wt. %) | Na-hyaluronate (wt. %) | Tensile strength (N/cm) | Tensile strength (N/cm$^2$) | Initial tear resistance (N) | Thickness before swelling (mm) | Swelling (thickness) after 20 min (%) | Swelling (length) after 20 min (%) | Water absorption after 20 min (ml/g) |
|---|---|---|---|---|---|---|---|---|---|---|
| A1 (start. m.) | 98.4 | 0.3 | 1.3 | 0.8 | 0.90 | 0.08 | — | — | — | — |
| Ex. 1 | 6.0 | 17.4 | 76.5 | 6.4 | 106 | 2.7 | 0.60 | 220 | −4 | 17 |
| Ex. 2 | 6.0 | 17.4 | 76.5 | 11.6 | 386 | 1.8 | 0.30 | 390 | −3 | 20 |
| Ex. 3 | 6.1 | 17.4 | 76.5 | 8.7 | 435 | 1.4 | 0.20 | 130 | +7 | 11 |
| Ex. 4 | 6.4 | 17.4 | 76.2 | 8.8 | 1470 | 1.0 | 0.06 | 200 | −3 | 5 |
| B1 (start. m.) | 98.5 | 0.2 | 1.3 | 1.0 | 1.8 | 0.05 | — | — | — | — |
| Ex. 5 | 6.3 | 13.4 | 80.3 | 9.0 | 69 | 1.4 | 1.3 | 140 | −3 | 18 |
| Ex. 6 | 6.3 | 13.4 | 80.3 | 6.4 | 188 | 1.0 | 0.34 | 520 | −3 | 18 |
| Ex. 7 | 6.5 | 13.4 | 80.1 | 14.1 | 881 | 1.3 | 0.16 | 360 | +7 | 5 |
| Ex. 8 | 7.1 | 13.2 | 79.6 | 19.5 | 3250 | 6.1 | 0.06 | 200 | +2 | 3 |
| A2 (start. m.) | 98.5 | 0.2 | 1.3 | 0.4 | 0.56 | 0.04 | — | — | — | — |
| Ex. 9 | 6.2 | 13.1 | 80.7 | 5.1 | 283 | 0.9 | 0.18 | 670 | −3 | 12 |
| Ex. 10 | 6.5 | 13.1 | 80.4 | 26.1 | 3260 | 0.8 | 0.08 | 350 | +10 | 7 |
| B2 (start. m.) | 98.5 | 0.2 | 1.3 | 0.9 | 1.1 | 0.09 | — | — | — | — |
| Ex. 11 | 6.0 | 10.5 | 83.5 | 8.5 | 708 | 1.6 | 0.12 | 500 | +1 | 9 |
| Ex. 12 | 6.3 | 10.5 | 83.2 | 9.3 | 930 | 1.9 | 0.10 | 100 | ±0 | 2 |

The above presented test results clearly demonstrate the significantly improved strength properties of the dry hyaluronic acid plates and sheets, respectively, in comparison with the gel plates used as starting material.

The invention is, of course, not restricted to the above described embodiments and examples, but it may be varied and modified in many ways within the scope of the accompanying claims.

What is claimed is:

1. A shaped article based upon cross-linked, possibly derivatized hyaluronic acid or a salt thereof, which in a substantially unswollen water-swellable state has a dry matter content of at least 65 percent by weight and a tensile strength greater than 100 N/cm$^2$.

2. An article according to claim 1, wherein the dry matter content is 85-98 percent by weight.

3. An article according to claim 1, having a tensile strength greater than 1000 N/cm$^2$.

4. An article according to claim 1, which is plate- or sheet-shaped.

5. An article according to claim 1 which is produced by compressing a gel of cross-linked, possibly derivatized hyaluronic acid or a salt thereof between two pressure surfaces.

6. An article according to claim 5 wherein at least one pressure surface has a sufficient porosity to permit passage of the fluid squeezed out from the gel through the pressure surface.

7. An article according to claim 5 wherein said compression is effected with a pressure of 10-10$^5$ kPa.

8. An article according to claim 7 wherein said compression is effected with a pressure of 200-1000 kPa.

9. An article according to claim 5 comprising the additional step of heat treating the dried product obtained at a temperature of about 50° to about 150° C.

10. An article according to claim 1 which is produced by subjecting a gel of cross-linked, possibly derivatized hyaluronic acid or a salt thereof to a vacuum permitting freeze drying.

11. An article according to claim 10 wherein the gel material is supported on a porous support to be subjected to said vacuum over substantially the entire gel surface.

12. An article according to claim 10 comprising the additional step of compressing the dried product obtained.

13. An article according to claim 12 wherein the dried product is compressed at a pressure of 10-10$^5$ kPa.

14. An article according to claim 12 comprising the additional step of heat treating the dried product obtained at a temperature of about 50° to about 150° C.

* * * * *